(12) United States Patent
Kusiek et al.

(10) Patent No.: US 11,768,188 B2
(45) Date of Patent: Sep. 26, 2023

(54) CARTRIDGE-BASED SENSOR SYSTEM FOR MONITORING PROPERTIES OF FIELD SOILS AND WASTEWATER

(71) Applicant: CLIMATE LLC, Saint Louis, MO (US)

(72) Inventors: Jordan Kusiek, Beaverton, OR (US); Andreas Wenzel, Seattle, WA (US); Calden Nathaniel Carroll Stimpson, Alameda, CA (US)

(73) Assignee: CLIMATE LLC, Saint Louis, MO (US)

( * ) Notice: Subject to any disclaimer, the term of this patent is extended or adjusted under 35 U.S.C. 154(b) by 745 days.

(21) Appl. No.: 16/659,969

(22) Filed: Oct. 22, 2019

(65) Prior Publication Data

US 2020/0132655 A1   Apr. 30, 2020

Related U.S. Application Data

(60) Provisional application No. 62/750,145, filed on Oct. 24, 2018.

(51) Int. Cl.
*G01N 33/24* (2006.01)
*G01N 33/18* (2006.01)
(Continued)

(52) U.S. Cl.
CPC ............ *G01N 33/24* (2013.01); *A01B 79/005* (2013.01); *A01G 25/16* (2013.01); *G01N 1/04* (2013.01);
(Continued)

(58) Field of Classification Search
CPC .......... G01N 33/24; G01N 1/04; G01N 1/10; G01N 27/333; G01N 33/188; G01N 2033/245; A01B 79/005; A01G 25/16
See application file for complete search history.

(56) References Cited

U.S. PATENT DOCUMENTS

2006/0221741 A1   10/2006 Jain et al.
2007/0277879 A1 * 12/2007 Anderson .............. A01G 25/16
                                                                137/78.3
(Continued)

OTHER PUBLICATIONS

The International Searching Authority, Search Report In application No. PCT/US2019/057335, dated Jan. 14, 2020, 16 pages.
(Continued)

*Primary Examiner* — Benjamin R Schmitt
(74) *Attorney, Agent, or Firm* — Harness, Dickey & Pierce, P.L.C.

(57) ABSTRACT

In an embodiment, a sensor system and a method for monitoring properties of field soils and wastewater are described. In an embodiment, a sensor system comprises a cartridge system implemented in an integrated circuit. The cartridge system comprises a chemical sensor and a computer processor coupled to the chemical sensor. The chemical sensor is configured to receive a sample of a test material such as soil or wastewater. Based on the sample of the test material, the chemical sensor determines a measure of a property in the test material. The computer processor receives, from the chemical sensor, the measure of the property in the test material, and computes, based on, at least in part, the measure of the property in the test material, a concentration level of the property in the test material. Based on the concentration level of the property in the test material, the computer processor generates an output that includes the concentration level. In an embodiment, the concentration level of the property in the test material is provided to a computer-based controller that controls agricultural equipment executing an agricultural prescription in an agricultural field.

18 Claims, 12 Drawing Sheets

(51) Int. Cl.
   *G01N 1/04* (2006.01)
   *G01N 27/333* (2006.01)
   *A01G 25/16* (2006.01)
   *A01B 79/00* (2006.01)
   *G01N 1/10* (2006.01)

(52) U.S. Cl.
   CPC .............. *G01N 1/10* (2013.01); *G01N 27/333* (2013.01); *G01N 33/188* (2013.01); *G01N 2033/245* (2013.01)

(56) References Cited

U.S. PATENT DOCUMENTS

| | | | |
|---|---|---|---|
| 2013/0324421 A1* | 12/2013 | Rothberg | C12Q 1/6869 506/2 |
| 2014/0170645 A1 | 6/2014 | Jovanovich et al. | |
| 2015/0323491 A1 | 11/2015 | Miller et al. | |
| 2015/0353919 A1 | 12/2015 | Mielke et al. | |
| 2016/0033412 A1 | 2/2016 | Tan et al. | |
| 2017/0169523 A1 | 6/2017 | Xu et al. | |
| 2017/0176255 A1 | 6/2017 | Nciri | |
| 2017/0248494 A1 | 8/2017 | Miller et al. | |
| 2019/0101505 A1* | 4/2019 | Liu | G01N 1/08 |

OTHER PUBLICATIONS

Current Claims in application No. PCT/US2019/057335, dated Jan. 2020, 4 pages.

* cited by examiner

Fig. 2
(a)
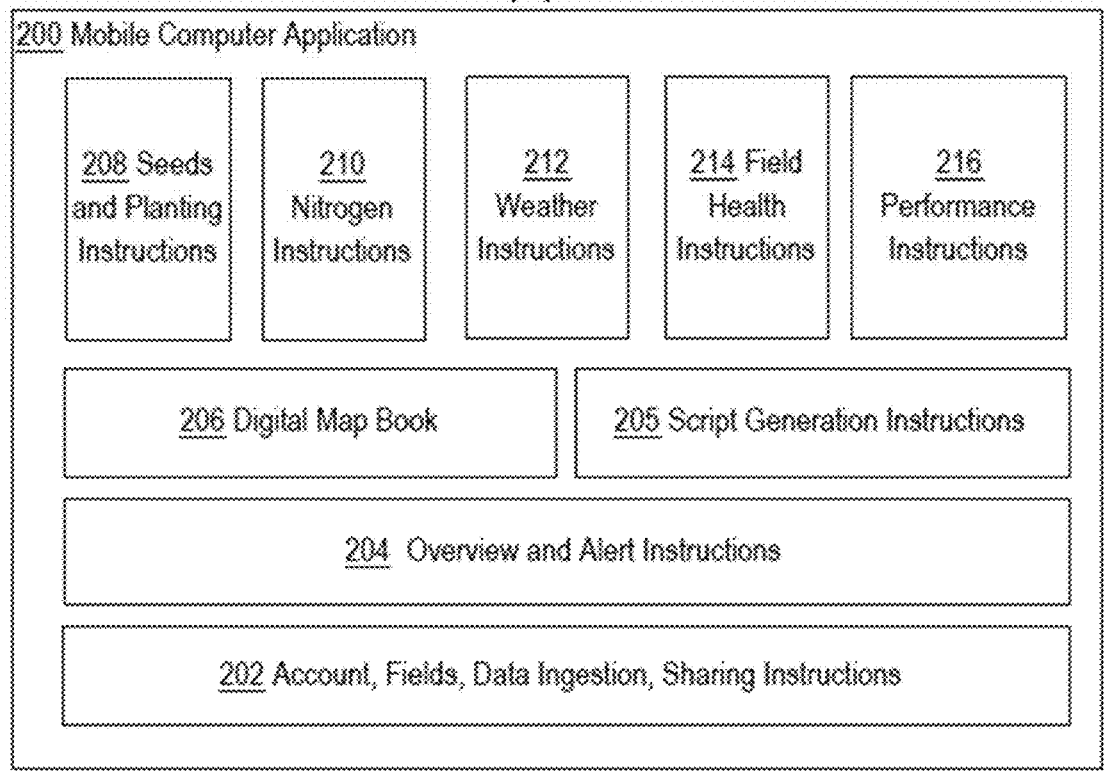
(b)
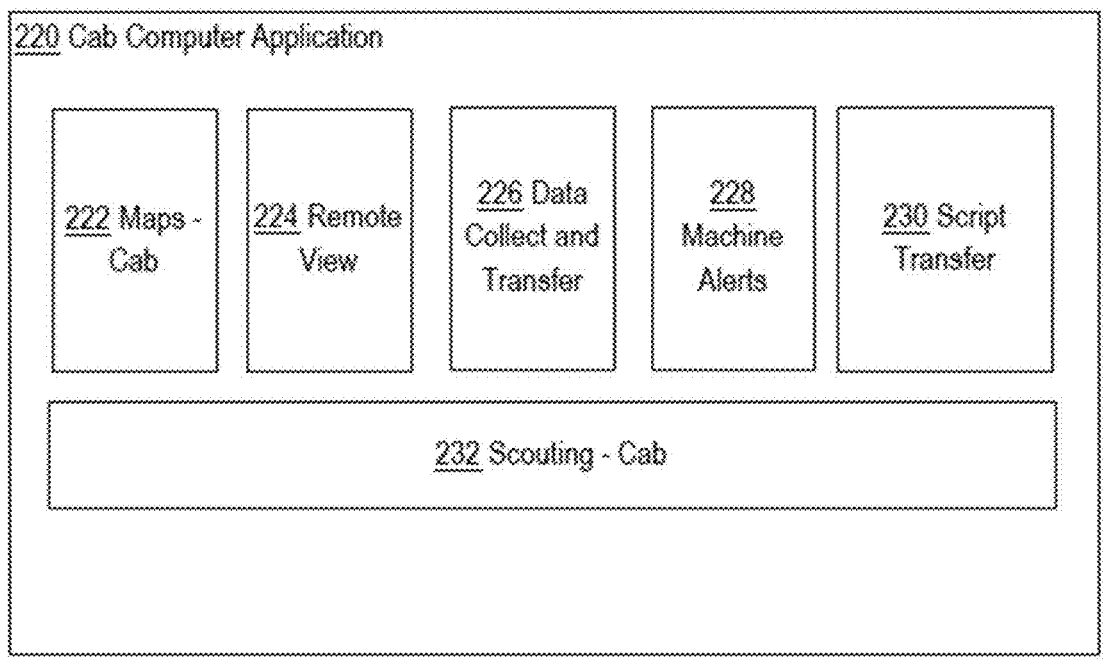

Fig. 6

CARTRIDGE-BASED SENSOR SYSTEM FOR MONITORING PROPERTIES OF FIELD SOILS AND WASTEWATER

BENEFIT CLAIM

This application claims the benefit under 35 U.S.C. § 119(e) of provisional application 62/750,145, filed Oct. 24, 2018, the entire contents of which is hereby incorporated by reference for all purposes as if fully set forth herein. The applicants hereby rescind any disclaimer of claim scope in the parent applications or the prosecution history thereof and advise the USPTO that the claims in this application may be broader than any claim in the parent applications.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015-2019 The Climate Corporation.

FIELD OF THE DISCLOSURE

The present disclosure relates to soil and water content measurements and particularly to using sensors implemented in integrated electronic cartridges to measure property concentration in test materials such as soil, water, and wastewater.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Further, it should not be assumed that any of the approaches described in this section are well-understood, routine, or conventional merely by virtue of their inclusion in this section.

Monitoring the amounts of nutrients in soil or wastewater allows crop growers to maintain the healthy soil. The monitoring process is, however, difficult because the amounts of nutrients in soil or water vary from one location to another, and the amounts vary with the sampling time, environmental conditions, and soil or water physical characteristics.

Nitrate measurements in soil or water have been achievable for some time. One approach for measuring a concentration level of nitrate in soil involves collecting a soil sample and sending the soil sample to a laboratory, which responds with a measurement of the nitrate concentration level within a few weeks. The time delay is, however, undesirable because the nitrate concentration level in soil can change quickly as the nitrate leaches from the soil over time, and at the time the measurement is received from the laboratory, the measurement may be inaccurate. The measurement may be inaccurate also because the amount of nitrate decreases by several folds during the shipment of the soil sample to the laboratory. Thus, at the time the measurement is received, the measurement rarely reflects a current nitrate concentration level in the soil.

SUMMARY

The appended claims may serve as a summary of the disclosure.

BRIEF DESCRIPTION OF THE DRAWINGS

In the drawings:

FIG. 2 depicts two views of an example logical organization of sets of instructions in main memory when an example mobile application is loaded for execution.

FIG. 6 depicts an example embodiment of a spreadsheet view for data entry.

DETAILED DESCRIPTION

Figure 1:
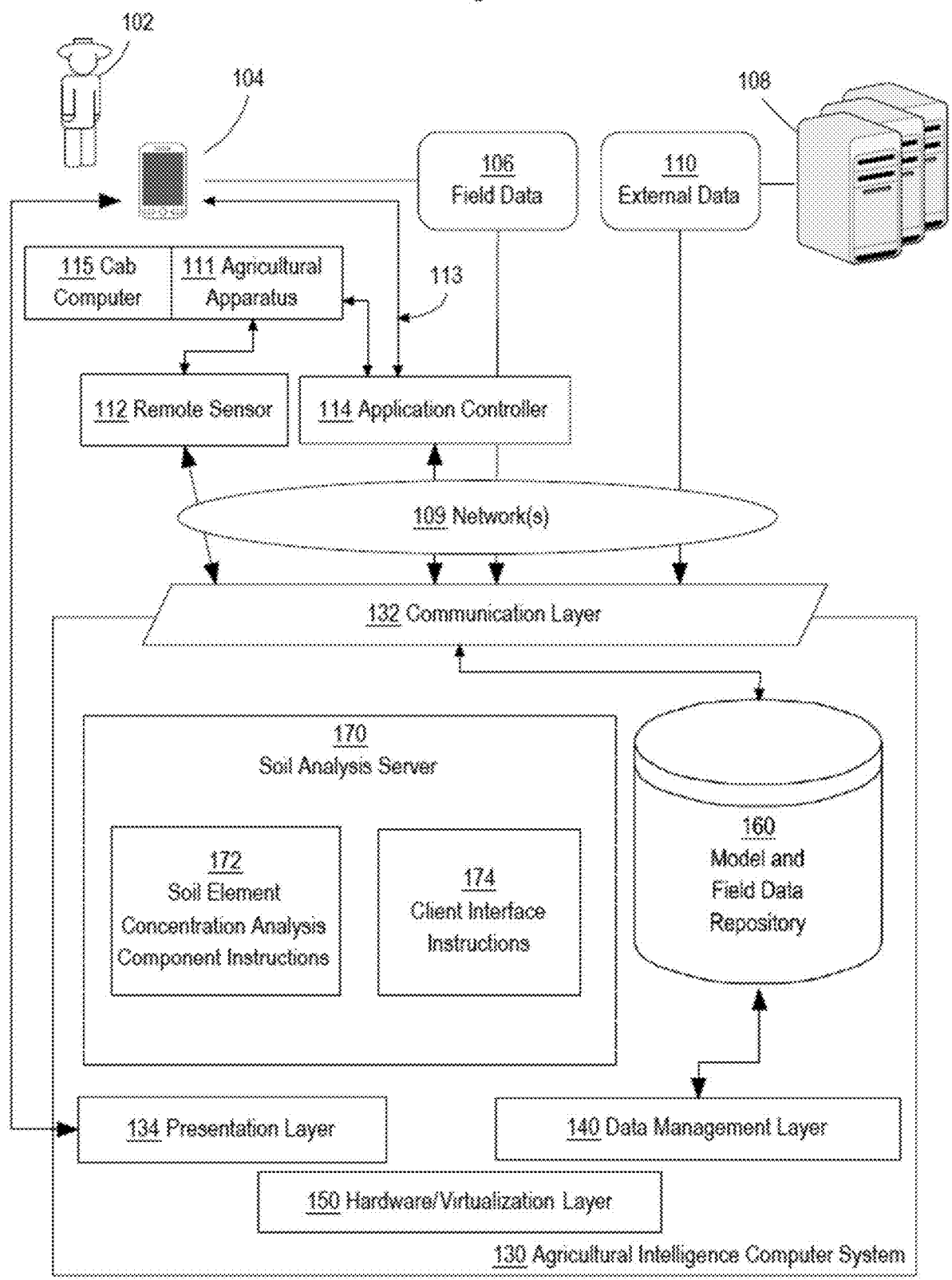
FIG. 1 depicts an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:

1. GENERAL OVERVIEW
2. EXAMPLE AGRICULTURAL INTELLIGENCE COMPUTER SYSTEM
   2.1. STRUCTURAL OVERVIEW
   2.2. APPLICATION PROGRAM OVERVIEW
   2.3. DATA INGEST TO THE COMPUTER SYSTEM
   2.4. PROCESS OVERVIEW—AGRONOMIC MODEL TRAINING
   2.5. SOIL ANALYSIS
   2.6. IMPLEMENTATION EXAMPLE—HARDWARE OVERVIEW
3. CARTRIDGE-BASED SENSOR SYSTEM FOR MONITORING PROPERTIES OF FIELD SOILS AND WASTEWATER
   3.1. SYSTEM OVERVIEW
      3.1.1. CHEMICAL SENSOR
      3.1.2. COMPUTER PROCESSOR
      3.1.3. RESULTS
   3.2. PROCESS OVERVIEW
   3.3. EXAMPLE IMPLEMENTATIONS
      3.3.1. HANDHELD DEVICES
      3.3.2. IN-FIELD PROBES
      3.3.3. ON-THE-GO MEASURING DEVICES
4. EXAMPLE SENSOR CARTRIDGE
5. EXTENSIONS AND ALTERNATIVES
6. BENEFITS OF CERTAIN EMBODIMENTS

1. General Overview

A cartridge-based sensor system implemented in an integrated electronic circuit for monitoring properties of field soils and/or wastewater is described. The system may be used to determine concentration levels of properties such as nitrate, chloride, phosphorus, chlorine, or pH in soil and/or water.

In an embodiment, the cartridge-based sensor system is implemented in an integrated circuit, also referred to as a chip. The sensor system may be enclosed in a sealed cartridge, and the cartridge may be integrated with a portable physical device, such as a handheld device, an in-field physical probe, or an on-the-go measuring device. Because the cartridge-based sensor system is portable, the system may be used to measure nutrient concentration levels at any location and at any time. The cartridge-based sensor system overcomes the shortcomings of the conventional systems that require sending the soil or water samples to laboratories and receiving the results on a delayed basis.

In an embodiment, a cartridge-based sensor system comprises a chemical sensor, a computer processor coupled to the sensor, and a power source providing electrical charge to both the sensor and the processor. The chemical sensor may be configured to receive a sample of a test material such as soil or water. Based on the sample, the sensor may determine a measure of a property in the test material. This may include determining a measure of nitrate, chloride, phosphorus, chlorine, or ph.

The measure may be provided to the computer processor for processing. Upon receiving the measure, the computer processor may compute a property concentration level in the test material. The concentration level may be computed based on the property measure provided by the sensor and based on an approximate size of the sample. The processor may also use data conversion tables and data specific to the test material.

Based on the property concentration information, the computer processor may generate output and provide the output to output devices. The output may include the concentration level information and, optionally, some information about the chemical sensor.

The information about the sensor may include, for example, information about a universally unique identifier ("UUID") of the sensor. The UUID information may be provided as part of output generated by the computer processor to output devices and may be used by the output devices to identify a type and a location of the sensor and the sensor system.

A location of the sensor may be determined based on the received UUID and a mapping between the UUIDs of sensors and the geographical locations at which the sensor systems are installed or used. Upon receiving the output that includes, for example, nitrate concentration level information and UUID information of a sensor, an output device may use the mapping and the UUID information to determine the location of the sensor system. Then, the output device may associate the nitrate concentration level information with the location of the sensor, generate a graphical representation of the association, and cause displaying the graphical representation on a display of the output device. The output device, or devices, may repeat the process each time the device receives output data from the same sensor or different sensors. For example, when the output device receives several outputs from several sensor systems, the output device may process each output by determining a corresponding UUID of a sensor, determining a location of the sensor based on the UUID and the mapping, associating the property concentration level information with the location, and displaying a graphical representation of the association on a display of the output device. The output device may update the graphical representation each time new output is received from the sensor systems installed throughout a field, and the updated graphical representation may form a comprehensive map of property concentration levels throughout the field. The map may depict, for example, concentration levels of nitrate, chlorine, pH, phosphorus, or other matter throughout the field, and may be used to improve agricultural and irrigation practices for the field.

The cartridge-based sensor system is a convenient and accurate tool for performing in situ and in real time nutrient and chemical analysis of soil and water. The sensor system may be configured to determine concentration levels of soil/water properties as soon as the soil/water samples are in contact with the cartridge. For example, if the sensor system is configured to detect nitrate and is installed in a handheld device, then the system may compute a nitrate concentration level in the soil as soon as the handheld device is inserted into the soil.

The ability to perform the content analysis of soil/water in real time provides convenience and versatility. For example, a crop grower may use the sensor system implemented in a handheld device to test a concentration level of nitrate in the field soil as frequently as needed to monitor the rapidly changing levels of the nitrate in the soil. Based on the monitoring, the grower may modify fertilization prescriptions for the field as frequently as needed.

In an embodiment, a cartridge-based sensor system and a corresponding method for providing nutrient concentration level information for field soil is used by agricultural researchers and developers working in technological centers. The researchers may use the provided nutrient concentration measurements to develop new seed varieties, enhance fertilization techniques, and develop enhancements to irrigation technologies. The nutrient concentration information may be also used to monitor the fields with a high vulnerability to chemical pollution, and to develop strategies and environment-aware practices for handling the soil nutrient losses.

In an embodiment, the nutrient concentration information for an agricultural field is used by agricultural companies and researchers to generate and update a data repository that stores information about properties of the fields. The data repository may be implemented in a computer server or a cloud system accessible to the companies. The data repository may be indexed using UUIDs of sensors of the sensor systems installed and used in the fields. When output data is provided by a sensor system to the data repository, the output data may be automatically or manually by the researchers time-stamped and parsed to extract nutrient concentration information and UUID information of the sensor. Then, the nutrient concentration information may be stored in data records indexed in the data repository using the UUID of the sensor. The data repository may be queried for data by the researchers and crop growers.

The nutrient concentration information may be provided directly to crop growers. The provided information may be used to assist the growers to manage agricultural fields. For example, the provided information may be used to help a grower to determine optimal schedules for cultivating a field, appropriate amounts of fertilizer for the filed, and recommended timetables for applying fertilizers to the field. The provided information may be also used to select seed hybrids that may produce optimal yields from the fields.

In an embodiment, the nutrient concentration information for a field is provided to a computer-based controller that controls agricultural equipment operating in the field. For example, the information that includes both nitrate concentration information for the soil and an UUID of the chemical sensor that determined the nitrate concentration in the soil may be used by a computer-based controller installed on a fertilizer machine to either increase or decrease the amount of the fertilizer as the fertilizer machine applies the fertilizer to the soil.

2. Example Agricultural Intelligence Computer System 2.1 Structural Overview

FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seeds), seed population), (e) fertilizer data (for example, nutrient type (Nitrogen, Phosphorus, Potassium), application type, application date, amount, source, method), (f) chemical application data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 may have one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, aerial vehicles including unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines, harvesters, sprayers, and cultivators. Application controller 114 is communicatively coupled to agricultural intelligence computer system 130 via the network(s) 109 and is programmed or configured to receive one or more scripts that are used to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, Calif., is used. Sensor data may consist of the same type of information as field data 106. In some embodiments, remote sensors 112 may not be fixed to an agricultural apparatus 111 but may be remotely located in the field and may communicate with network 109.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a graphical screen display, such as a color display, that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object-oriented databases, distributed databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U. S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
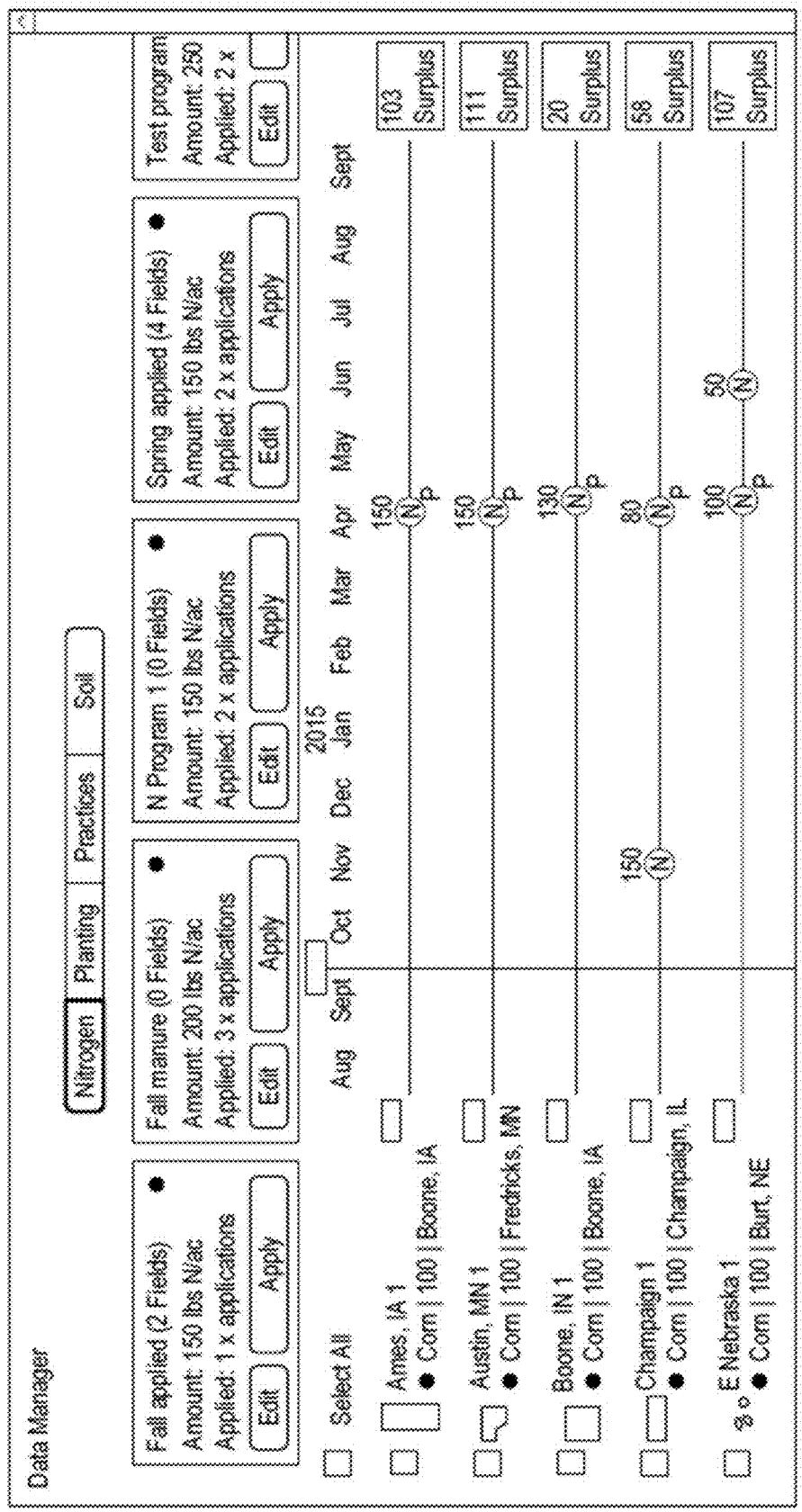
FIG. 5 depicts an example embodiment of a timeline view for data entry.

FIG. 5 depicts an example embodiment of a timeline view for data entry. Using the display depicted in FIG. 5, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Spring applied" program selected, which includes an application of 150 lbs N/ac in early April. The data manager may provide an interface for editing a program. In an embodiment, when a particular program is edited, each field that has selected the particular program is edited. For example, in FIG. 5, if the "Spring applied" program is edited to reduce the application of nitrogen to 130 lbs. N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Spring applied" program is no longer being applied to the top field. While the nitrogen application in early April may remain, updates to the "Spring applied" program would not alter the April application of nitrogen.

Figure 6:
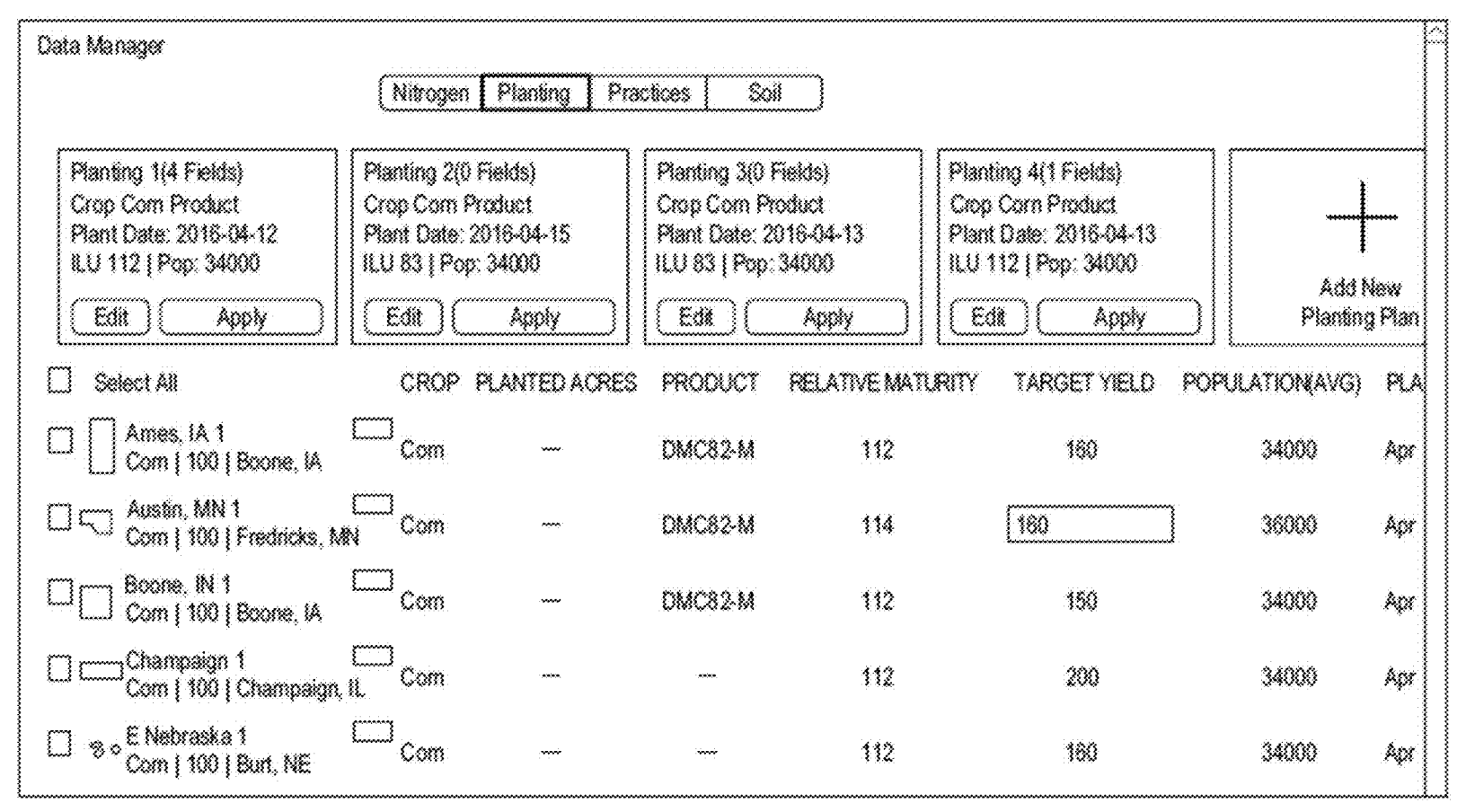

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In some embodiments, agricultural intelligence computer system 130 is programmed with or comprises a soil analysis server ("server") 170. The server 170 is further configured to comprise a soil property concentration analysis component 172 and a client interface 174. Each of the soil property concentration analysis component 172 and the client interface 174 may be implemented as sequences of stored program instructions. In some embodiments, the soil property concentration analysis component 172 is programmed to receive input data from one or more sources and output current concentration levels of a target analyte in the soil or recommendations for adjusting the current concentration levels. Input data to the soil property concentration analysis component 172 can include data generated by the cartridge-based sensor system for monitoring properties of field soils and wastewater introduced above and to be further discussed in in FIG. 8, which can comprise one or more of the agricultural apparatus 111, the application controller 114, and the remote sensor 112. An example of such data would be current nitrate concentration levels in certain soil samples. Additional input data can include data received from user computers, such as the field manager computing device 104 or the cab computer 115, or from the data server computer 108, or other data that have been stored in the model data field data repository 160, such as expected crop yield levels, soil nutrient loss history, historical weather reports or weather forecasts, or records of applying other types of soil nutrients. Output data from the soil property concentration analysis component 172 can include when and how to adjust concentration levels of certain soil nutrients or other elements as well as where such adjustment should be applied. Such data can be communicated to the user computers or other remote computers.

In some embodiments, the client interface 174 is configured to manage communication with the cartridge-based sensor system or a user computer over a communication network, through the communication layer 132. The communication can include receiving instructions to start real-time field measurements and desired soil condition or production level from a user computer, sending instructions to the mobile soil analysis system for performing real-time measurements of soil element concentration levels, receiving the soil measurements from the mobile soil analysis system, and sending results of analyzing the soil measurements with respect to the desired soil condition or production level to the user computer.

Each component of the server 170 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the soil element concentration analysis component 172 may comprise a set of pages in RAM that contain instructions which when executed cause performing soil element concentration analysis described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each of the components in the server 170 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130.

Figure 4:
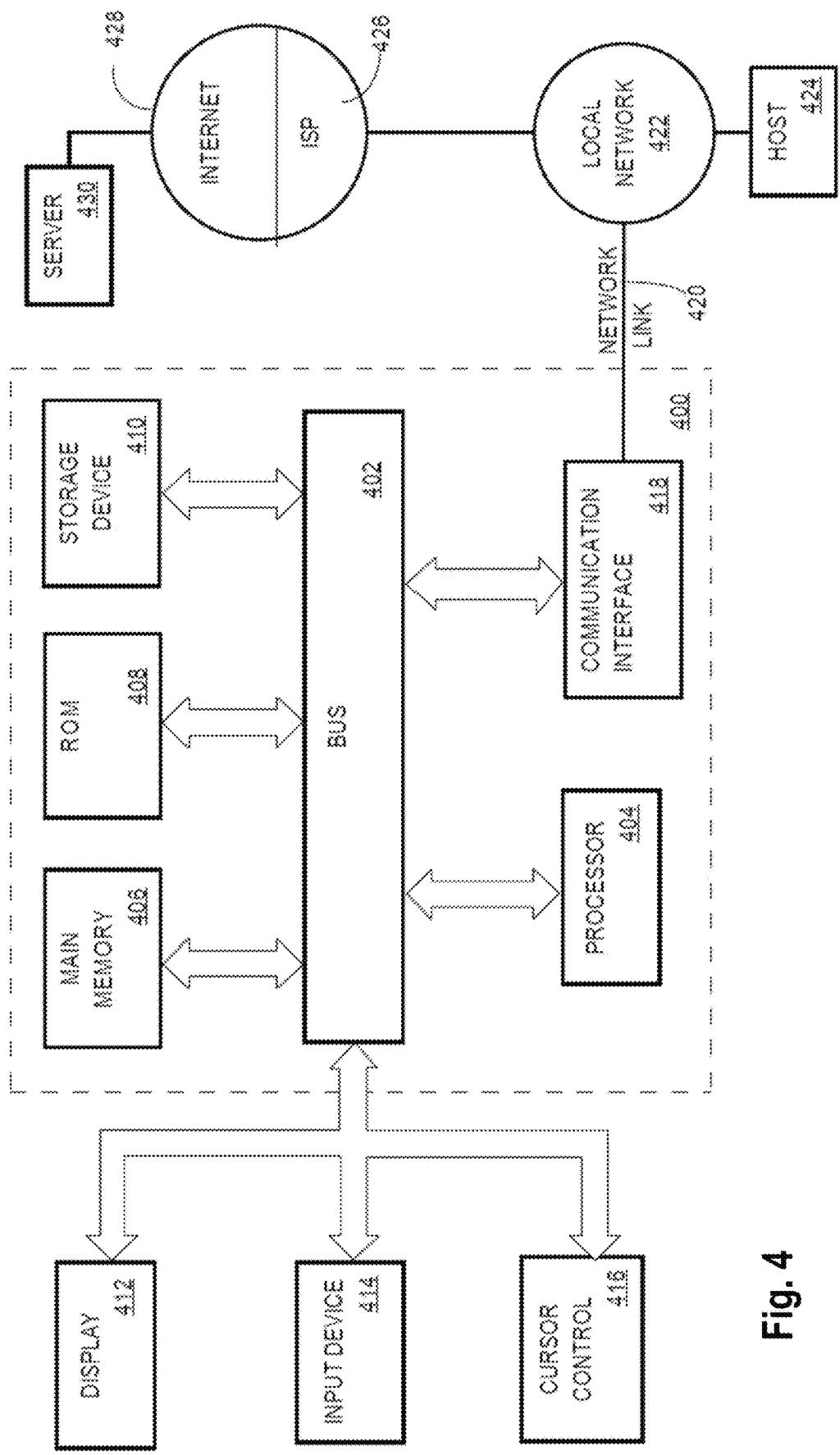
FIG. 4 is a block diagram that illustrates a computer system upon which an embodiment of the invention may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more smartphones, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML, and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), Wi-Fi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114 which include an irrigation sensor and/or irrigation controller. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account, fields, data ingestion, sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shapefiles, native data formats of third parties, and/or farm management information system (FMIS) exports, among others. Receiving data may occur via manual upload, email with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally, and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of fertilizer application zones and/or images generated from subfield soil data, such as data obtained from sensors, at a high spatial resolution (as fine as millimeters or smaller depending on sensor proximity and resolution); upload of existing grower-defined zones; providing a graph of plant nutrient availability and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields and/or zones that have been defined in the system; example data may include nitrogen application data that is the same for many fields and/or zones of the same grower, but such mass data entry applies to the entry of any type of field data into the mobile computer application 200. For example, nitrogen instructions 210 may be programmed to accept definitions of nitrogen application and practices programs and to accept user input specifying to apply those programs across multiple fields. "Nitrogen application programs," in this context, refers to stored, named sets of data that associates: a name, color code or other identifier, one or more dates of application, types of material or product for each of the dates and amounts, method of application or incorporation such as injected or broadcast, and/or amounts or rates of application for each of the dates, crop or hybrid that is the subject of the application, among others. "Nitrogen practices programs," in this context, refer to stored, named sets of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium), application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, yield differential, hybrid, population, SSURGO zone, soil test properties, or elevation, among others. Programmed reports and analysis may include yield variability analysis, treatment effect estimation, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the field manager computing device 104, agricultural apparatus 111, or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, Calif., may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or Wi-Fi-based position or mapping apps that are programmed to determine location based upon nearby Wi-Fi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus; other electromagnetic radiation emitters and reflected electromagnetic radiation detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

In an embodiment, sensors 112 and controllers 114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4. Process Overview—Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, fertilizer recommendations, fungicide recommendations, pesticide recommendations, harvesting recommendations and other crop management recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 3:
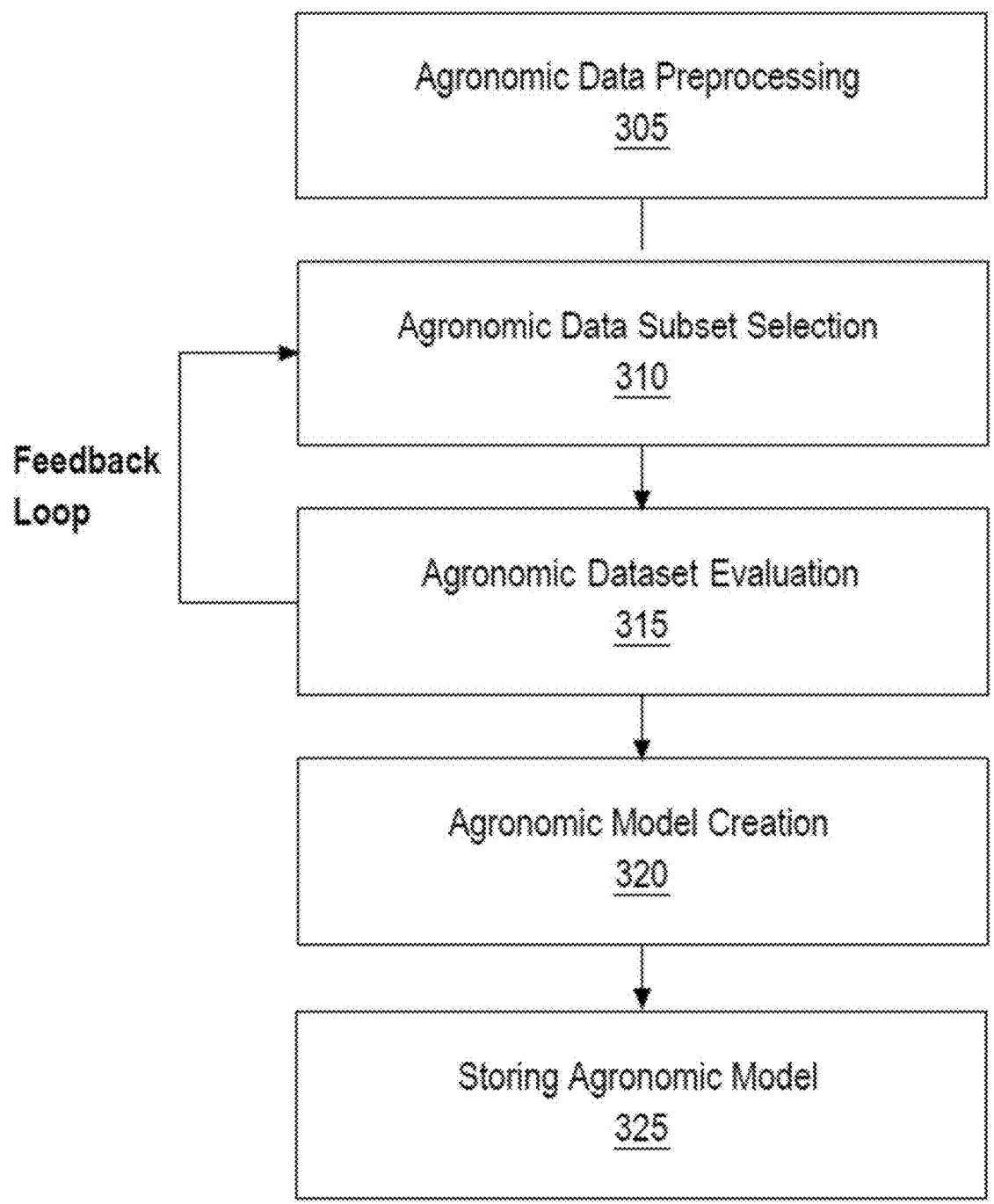
FIG. 3 depicts a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise, distorting effects, and confounding factors within the agronomic data including measured outliers that could adversely affect received field data values. Embodiments of agronomic data preprocessing may include, but are not limited to, removing data values commonly associated with outlier data values, specific measured data points that are known to unnecessarily skew other data values, data smoothing, aggregation, or sampling techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared and/or validated using one or more comparison techniques, such as, but not limited to, root mean square error with leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general-purpose microprocessor.

Computer system 400 also includes a main memory 406, such as a random-access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infrared data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infrared transmitter to convert the data to an infrared signal. An infrared detector can receive the data carried in the infrared signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated-services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world-wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

Figure 7:
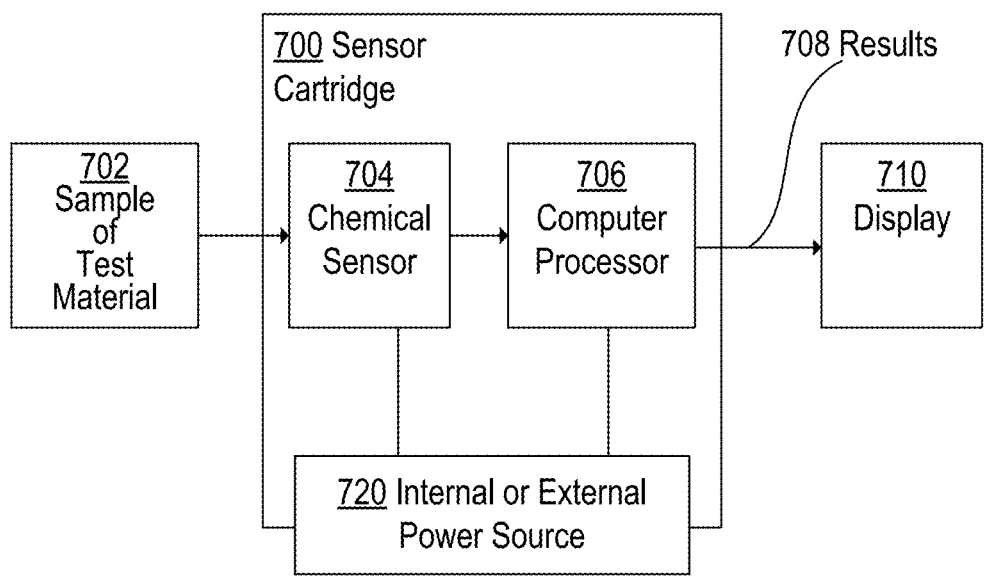
FIG. 7 depicts an example cartridge-based sensor system implemented in an integrated circuit and used to determine property concentration in field soils and wastewater.

3. Cartridge-Based Sensor System for Monitoring Properties of Field Soils and Wastewater 3.1. System Overview FIG. 7 depicts an example cartridge-based sensor system implemented in an integrated circuit and used to determine element concentration in field soils and wastewater. In the depicted example, a sensor system is enclosed in a sensor cartridge 700. Sensor cartridge 700 includes a sealed housing that protects components of the sensor system from moisture, dust, and other elements.

In an embodiment, sensor cartridge 700 is connected to an agricultural intelligence computer system 130 and/or the agricultural apparatus 111, such as the FIELDVIEW. The data from the sensor may be sent to the FIELDVIEW for processing, and/or may be used by the FIELDVIEW to derive various recommendations/assessments for the field soils.

Sensor cartridge 700 may include at least one chemical sensor 704, at least one computer processor 706, and an internal or external power supply source 720 for providing electrical charge to the sensors and processors. Chemical sensor 704 may be configured to perform a chemical analysis of a soil/water sample 702, while computer processor 706 may use the results of the chemical analysis to generate results 708. Power source 720 may be any type of a charge-providing component, including a conventional battery or a solar battery.

3.1.1. Chemical Sensor

Chemical sensor 704 may include several electronic components, such as electrodes, gates, temperature diodes, field-effect transistors, selective membranes, memory chips, and others. Chemical sensor 704 may have an associated UUID, and the UUID may be stored in the memory chip of the sensor. Chemical sensor 704 may be a silicon dioxide chip and may be configured to perform a chemical analysis of test samples provided to sensor cartridge 700.

A silicon dioxide chip is a field-effect transistor ("FET") which is a type of a metal-oxide-semiconductor field-effect transistor ("MOSFET"). The FET may be fabricated using a controller oxidation of silicon. The FET usually includes an insulated gate that is used to determine conductivity of the chip. The conductivity may be changed by modulating the amount of applied voltage, and the changes in the voltage may be used to amplify or switch electronic signals transmitted by the transistor. One of the advantages of the FET technology is that the transistor requires almost no input current to control the load current. Therefore, the transistor may be powered by a relatively small internal or external power source 720.

Chemical sensor 704 implemented in a silicon dioxide chip may include silicon substrates that are placed on a printed circuit board ("PCB") plate. The plate may have a 10-pin female Harwin connector. The substrates, the plate and the connector may be enclosed in cartridge 700, and cartridge 700 be covered, or coated, using epoxy or another sealer to allow only the pins of the connector protrude the cartridge.

In an embodiment, chemical sensor 704 is configured to perform a chemical analysis of test samples using diodes and chemical receptors for determining, for example, levels of nitrate in the samples. This may be performed by applying a so-called ion-force to the diodes and receptors of chemical sensor 704 and measuring the ions current between the diodes. The relationship between the current of ions and the diodes and a measure of nitrate in the test sample usually corresponds to a logarithmic function.

In an embodiment, chemical sensor 704 is configured to receive, or otherwise detect, a sample 702 of a test material, and determine a measure of a property in sample 702. For example, if chemical sensor 704 is configured to detect nitrate in sample 702, then upon receiving, or otherwise detecting, sample 702, chemical sensor 704 may determine a measure of nitrate in sample 702.

Sample 702 may be a sample of any material or matter. For example, sample 702 may be a field soil sample. Sample 702 may be detected by chemical sensor 704 upon a contact with the sample. Sample 702 may also be a water sample that can be detected by chemical sensor 704 once sensor cartridge 700 is submerged in a pool of water, a flask with water, an irrigation system reservoir, or any other vessel containing water. Sample 702 may also be a wastewater sample that can be detected by chemical sensor 704 once sensor cartridge 700 is submerged in a wastewater reservoir.

3.1.2. Computer Processor

Computer processor 706 is enclosed in sensor cartridge 700 and may be coupled to chemical sensor 704 included in cartridge 700. In some embodiments, computer processor 706 may be part of chemical sensor 704 and may be fabricated on the same chip as chemical sensor 704.

Computer processor 706 may be configured to receive data from chemical sensor 704 and process the received data. The processing may include converting data representing a measure of a particular property in sample 702 to a concentration level of the property in sample 702. The conversion may include determining a size of the sample, normalizing the measure of the property in sample 702, and determining the concentration level of the property within a standardized range and/or using standardized units. For example, a nitrate concentration level in sample 702 may be expressed as a count of nitrate parts per million ("PPM") in a standardized size of sample 702.

3.1.3. Results

Results 708 may include information about a concentration level of a property in sample 702. In some embodiments, results 708 may also include a UUID of chemical sensor 704.

Results 708 may be displayed on a display 710. Display 710 may be configured in a device that is separate from sensor cartridge 700 and may be supported by a separate computing device (not depicted in FIG. 7). For instance, display 710 may be implemented in a mobile device that carries sensor cartridge 700. For example, if sensor cartridge 700 is implemented in a handheld device, then display 710 may be part of the handheld device. The format and graphical representation of results 708 displayed on display 710 may vary and may depend on the display capabilities of display 710.

In some embodiments, results 708 are transmitted to a data repository, a cloud storage system, or other storage system. Results 708 stored in, for example, the data repository, may be used to build a comprehensive database of information about agricultural fields, and to build a data bank of agricultural data that can be used by researchers, crop growers, and agricultural industries.

In some embodiments, results 708 are further analyzed and used to generate recommendations for users. For example, results 708 may include additional data, such a UUID of chemical sensor 704, and may be transmitted to another computer system (not depicted in FIG. 7). That computer system may use results 708 to create a nitrate map for the field to indicate the nitrate concentration level for the entire field or for sub-regions of the field. Based on the nitrate map, the computer system may generate agricultural recommendations for the field. To generate the recommendations, the computer system may also use additional data such as weather reports, fertilization histories, target yield amounts, moisture indicators, or pollutant updates. The computer system may then transmit the recommendations to a central server, a user computer, or directly to a computer-based controller that controls agricultural equipment.

3.2. Process Overview

Figure 8:
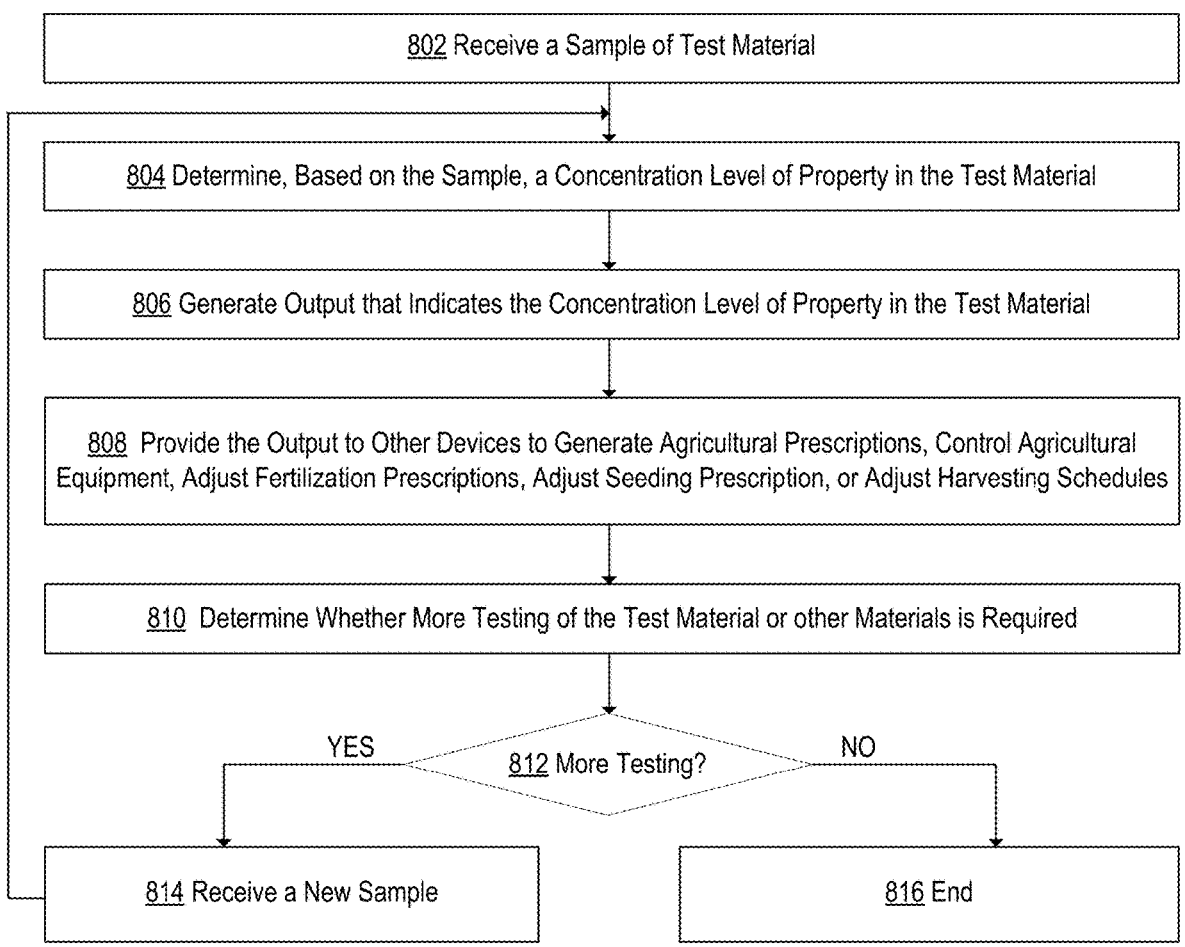
FIG. 8 depicts an example process that uses a sensor-based system implemented in an integrated circuit to determine property concentration in field soils and wastewater.

FIG. 8 depicts an example process that uses a sensor-based system implemented in an integrated circuit to determine property concentration in field soils and wastewater. The example process may be executed by components of cartridge-based sensor system 700, depicted in FIG. 7. For the clarity of the description, cartridge-based sensor system 700 performing steps described in FIG. 8 is referred to herein as a sensor system.

In step 802, a sensor system receives a sample of test material. The sensor system may receive the sample when chemical sensor 704, depicted in FIG. 7, is in contact with a soil sample or a water sample. For example, if sensor cartridge 700, depicted in FIG. 7, is inserted into soil, then chemical sensor 704 may touch the soil, and thus receive a soil sample. According to another example, if sensor cartridge 700 is at least partially submerged in a wastewater container, then chemical sensor 704 may detect the water surrounding sensor cartridge 700.

In step 804, the sensor system determines a concentration level of a property in the soil sample. This may include determining, using chemical sensor 704, a measure of the property in the soil sample, and then computing, using computer processor 706, a concentration level of the property in the soil sample based on the measure.

Computer processor 706 may compute the property concentration level in the sample based on the provided measure, an approximate size of the sample, conversion tables and data specific to the sample itself. Depending on the specification of chemical sensor 704, the property concentration level may pertain to a level of nitrate, phosphorus, chlorine, pH, potassium, or another element present in the sample.

In step 806, the sensor system generates output that indicates the concentration level of the property in the sample. The output may also include a UUID of chemical sensor 706. Computer processor 706 may retrieve the UUID from a memory chip of chemical sensor 704 and generate a data object that includes the property concentration level information and the UUID information. The data object may be stored in a memory cache or a memory unit of the sensor system, and the content of the data object may be retrieved from the memory and provided as results 708, depicted in FIG. 7.

In an embodiment, the sensor system transmits the output to output devices, such as computer servers, user computers, and computer-based controllers. For example, the output may be transmitted to a data repository maintained by a research laboratory server or to a mobile device owned by a crop grower. The output may be used by researchers and crop growers in a variety of applications, as described below.

In step 808, the output is provided to computer servers and/or user computers to improve and enhance agricultural practices, such as fertilizing, seeding, or harvesting. For example, the output may be used to generate or modify agricultural prescriptions for the field. If the output includes, for example, information about a nitrate concentration level in a field, then the output may be used to determine, or adjust, an amount of the nitrogen-based fertilizer to be applied to the field to compensate for the nitrate leaching occurred over time.

The output may be transmitted to a computer-based controller that controls agricultural equipment such as seeders and planters. For example, the output that includes information indicating some ponding water in a field plot may be transmitted to a computer-based controller of a seeder and used by the controller to instruct the seeder to avoid dispensing the seeds in that plot of the field.

In step 810, the sensor system tests whether more testing of the test material or other materials is required. The testing may include providing the test material to the sensors installed in the sensor system and collecting readings from the sensors. The sensors may, for example, expose the test material to chemical reaction with the chemicals stored in the sensors, and provide a measure the results of the chemical reaction. If more testing is required, then the sensor system proceeds to performing step 814, in which the sensor system receives a new sample of either the same material or a different material and proceeds to performing step 804. However, if no more testing is required at this time, then in step 816 the sensor system stops executing.

3.3. Example Implementations 3.3.1. Handheld Devices

Figure 9A:
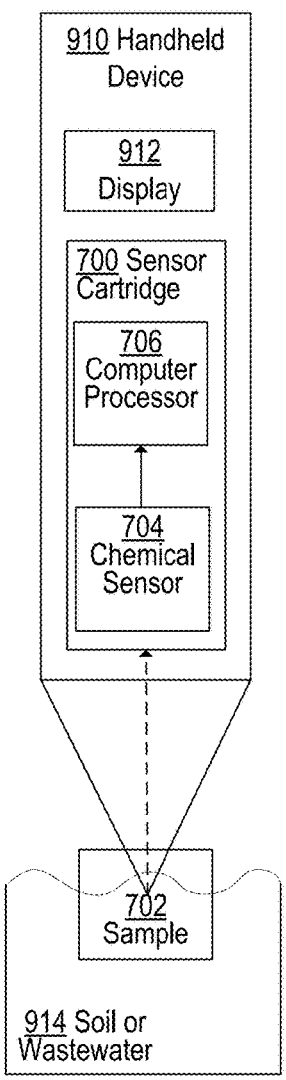
FIG. 9A depicts an example sensor system implemented in an integrated circuit incorporated into a handheld device and configured to determine property concentration in field soils and wastewater.

FIG. 9A depicts an example sensor system implemented in an integrated circuit incorporated into a handheld device and configured to determine property concentration in field soils and wastewater. In the depicted example, a sensor-based system is incorporated in a handheld device 910, which may be a portable device that is convenient to carry and use in a field or water.

In an embodiment, handheld device 910 comprises sensor cartridge 700 containing chemical sensor 704, computer processor 706, and internal or external power source (not depicted in FIG. 9A). Sensor cartridge 700 is described in FIG. 7. The process of generating output by components of sensor cartridge 700 is described in FIG. 8.

In some embodiments, handheld device 910 includes a display 912 that may be configured to display output data generated or obtained by computer processor 706. Handheld device 910 may also include a transceiver (not depicted in FIG. 9A) configured to establish communications connections between computer processor 706 and other computer systems (not depicted in FIG. 9A) and facilitate data exchange between computer processor 706 and other systems.

Handheld device 910 may be used to determine property concentration in field soils. For example, handheld device 910 may be inserted into a cavity created in soil, and once handheld device 910 is pushed into the cavity, soil sample 702 becomes in contact with handheld device 910. Upon detecting soil sample 702, the components of sensor cartridge 700 perform a chemical analysis of content of spoil sample 702. Results of the chemical analysis may include information about a concentration level of nitrate or other element in the soil.

Handheld device 910 may be also attached to an agricultural cultivator, and as the cultivator traverses the field, samples 702, of either soil or water, are detected by chemical sensor 704. Upon detecting soil samples 702, the components of sensor cartridge 700 may perform a chemical analysis of the samples.

Handheld device 910 may be used to determine property concentration in water. For example, handheld device 910 may be placed on a surface of the vessel containing water such as a swimming pool, an irrigation reservoir, a pond, and the like. As handheld device 910 floats on the surface, the components of sensor cartridge 710 may perform a chemical analysis of content of water sample 702. The analysis may include determining a chlorine concentration level in the water.

The results of the chemical analysis may be displayed on display 912, which may be equipped with any type of interface, including a graphical user interface.

If handheld device 910 is equipped with a transceiver (not depicted in FIG. 9A), then the results may be electronically transmitted to other computer systems (not depicted in FIG. 9A).

3.3.2. In-Field Probes

Figure 9B:
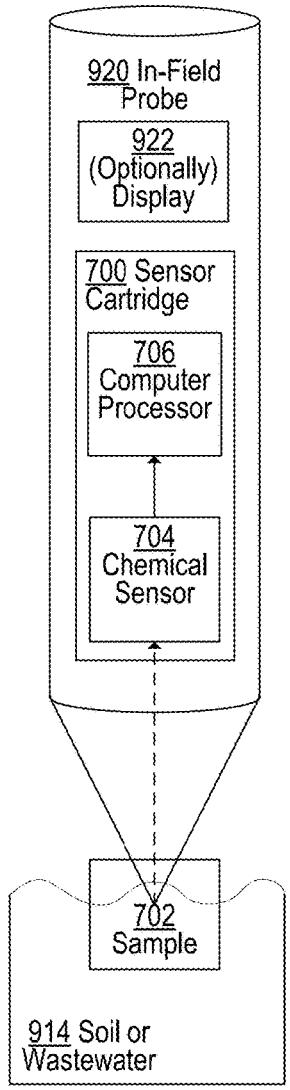
FIG. 9B depicts an example sensor system implemented in an integrated circuit incorporated into an in-field probe and configured to determine property concentration in field soils and wastewater.

FIG. 9B depicts an example sensor system implemented in an integrated circuit incorporated into an in-field probe and configured to determine property concentration in field soils and wastewater. In the depicted example, a sensor-based system is incorporated into an in-field probe 920 that may be either permanently inserted into soil, and adjustably inserted into soil. The adjustability provides many benefits since the properties of the soil are not homogeneous throughout the soil. For example, the properties of the soil at the soil depth of 6 inches may be different than the properties of the soil at the soil depth of 12 inches. In-field probe 920 may be permanently installed in a cavity created in field soil and used to determine property concentration in field soil by performing chemical analysis of sample 702. The location and position of in-field probe 920 may be adjusted over time depending on the type of concentration levels of soil samples are to be measured.

Depending on circumstances, either one in-field probe 920 is used, or a plurality of in-field probes 920 is used to measure property concentration of soil. For example, several in-field probes 920 may be used to measure property concentration in soil at different depths, different locations, and different times. Some in-field probes may be used to measure property concentration at various locations within the field; other in-field probes may be used to measure property concentration in irrigation systems, pond waters, and the like.

In an embodiment, in-field probe 920 comprises sensor cartridge 700 containing chemical sensor 704, computer processor 706, and internal or external power source (not depicted in FIG. 9B). Sensor cartridge 700 is described in FIG. 7, and the measuring process is described in FIG. 8.

In some embodiments, in-field probe 920 includes a display 922 that may be configured to display data generated or obtained by computer processor 706. In-field probe 920 may also include a transceiver (not depicted in FIG. 9A) configured to establish communications connections between computer processor 706 and other computer systems (not depicted in FIG. 9B) and facilitate data exchange between computer processor 706 and other systems.

In-field probe 920 may also include a computer-generated display for displaying output, or results, generated by chemical sensor 704 and computer processor 706.

A crop grower may use one or more in-field probes 920 to collect property concentration levels at different plots of an agricultural field and use the collected information to efficiently manage the field. For example, the grower may use the received information to vary the amounts of fertilizer used in the plots, and to adjust the fertilization schedules depending on the current level of nutrients in the plots.

3.3.3. On-the-Go Measuring Devices

Figure 9C:
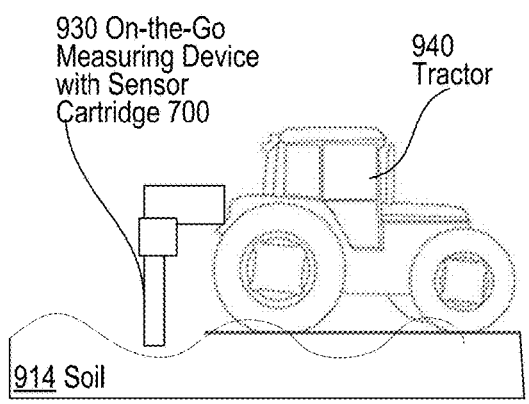
FIG. 9C depicts an example sensor system implemented in an integrated circuit incorporated into an on-the-go measuring device and configured to determine property concentration in field soils and wastewater.

FIG. 9C depicts an example sensor system implemented in an integrated circuit incorporated into an on-the-go measuring device and configured to determine property concentration in field soils and wastewater. In the depicted example, the sensor system is enclosed in sensor cartridge 700 which includes the components described in FIG. 7.

In an embodiment, sensor cartridge 700 is installed in an on-the-go measuring device 930. Measuring device 930 may be implemented as an attachment to a tractor 940 or any other agricultural vehicle. Tractor 940 may be any type of vehicle that is capable of moving while carrying sensor cartridge 700. Tractor 940 may be a planter or an all-terrain vehicle that may travel on the ground and may be operated via a motor, mechanically or manually.

As tractor 940 traverses a field, on-the-go measuring device 930 is submerged in the soil allowing sensor cartridge 700 to obtain soil samples and provide the samples to the components of sensor cartridge 700. For example, as the chemical sensor within cartridge 700 touches the soil, the sensor can determine a measure of a property of the soil. The computer processor within cartridge 700 may receive the measure and determine a property concentration level in the soil.

The concentration level information may be provided to computer servers and user devices and may be used by researchers and crop growers to develop and improve agricultural prescriptions for the field. For example, a crop grower may collect, from on-the-go measuring device 930, property concentration information for different plots of the field. As tractor 940 traverses the field, the crop grower driving the tractor may obtain the real time readings of, for example, the nitrate concentration levels for various plots of the field and use the obtained readings to determine amounts of nitrogen fertilizer to be applied to the plots. If the tractor also tows a machine configured to apply the nitrogen-based fertilizer to the field, then the nitrate concentration information provided by on-the-go measuring device 930 may be sent to a computer-based controller that can adjust the amounts of the fertilizer applied to the plots as tractor 940 traverses the field.

4. Example Sensor Cartridge

Figure 10A:
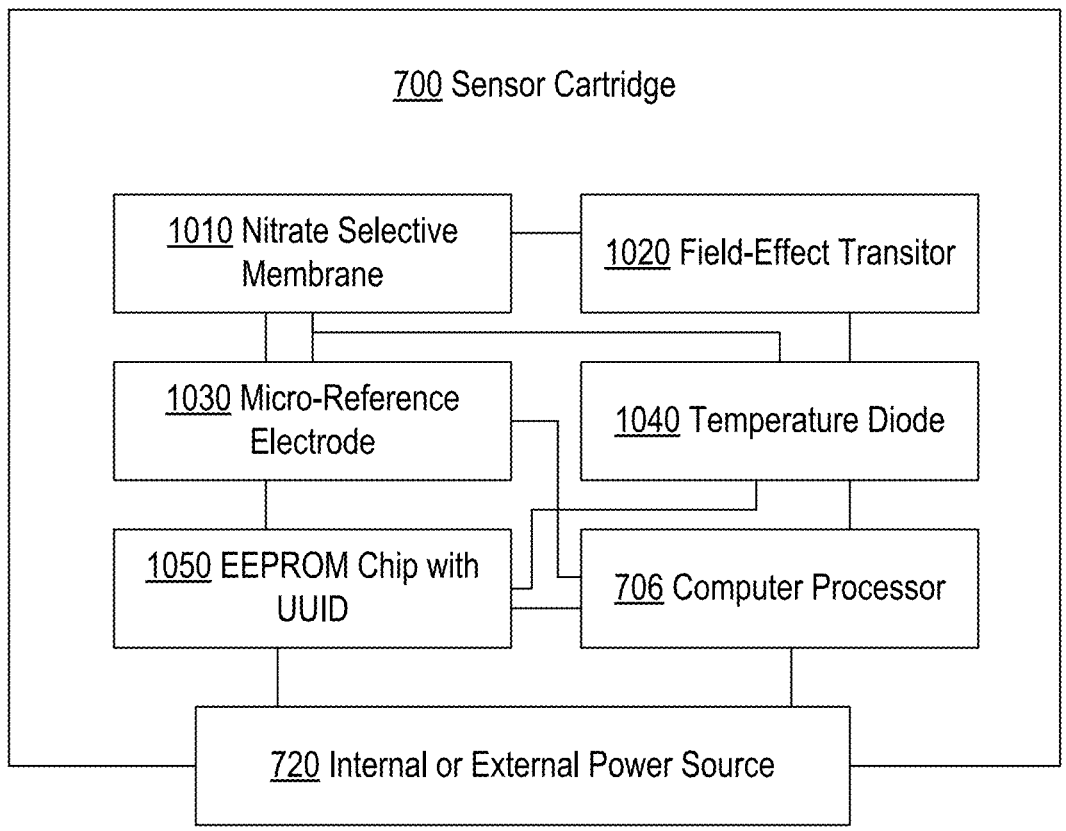
FIG. 10A depicts an example sensor cartridge that is implemented in an integrated circuit and that includes a sensor-based system configured to determine property concentration in samples of soil or water.

FIG. 10A depicts an example sensor cartridge 700 that is implemented in an integrated circuit and that includes a sensor-based system configured to determine property concentration in samples of soil or water. In the depicted example, sensor cartridge 700 comprises computer processor 706, internal or external power source 720, and components 1010-1050 that are part of a chemical sensor. Computer processor 706 and power source 720 are described in FIG. 7.

Components 1010-1050 include a nitrate selective membrane 1010, a field-effect transistor 1020, a micro-reference electrode 1030, a temperature diode 1040, and an electrically erasable programmable read-only memory (EEPROM) chip 1050 for storing, for example, a UUID of the chemical sensor. While components 1010 and 1040-1050 may be typical electronic components used in electronics, components 1020-1030 may be unique to the cartridge-based sensor system for monitoring properties in field soils and water.

In an embodiment, micro-reference electrode 1030 of the chemical sensor may be an ion selective electrode ("ISE"). An ISE is capable of direct moist soil sensing. For example, a nitrate ISE may be used to measure the concentration of nitrate ("$NO_3^-$") in water samples. The ISE can be either a traditional ISE which is based on liquid junction or a modern solid-state ISE which is based on solid junction. The ISE may be calibrated using prepared reagent-grade target analyte standards solutions, to ensure that the sensors are operating as expected.

Generally, an ISE converts the activity of a specific ion dissolved in a solution into an electrical potential. The ISE may include a processing unit that further converts the electrical potential measured for the target analyte into a readable concentration level. The obtained readable concentration level may be in the range of 0.1-14,000 PPM. Since the expected range of a soil element is usually in the range of 0-50 PPM, the measures provided by the chemical sensor need to be converted to the target soil range. This may be performed by computer processor 706.

In an embodiment, field-effect transistor 1020 is a chemically-sensitive field-effect transistor ("ChemFET"). A ChemFET is a transistor that can be used as a sensor for measuring chemical concentrations of elements in test samples. When the target analyte concentration changes, the current passing through the ChemFETs will change accordingly.

In sensor cartridge 700, the analyte solution separates the source and gate electrodes, and a concentration gradient between the solution and the gate electrode rises due to reactions of semi-permeable nitrate selective membrane 1010. The concentration gradient of the charged analyte ions creates a chemical potential between the source and gate electrodes, and the chemical potentials may be measured by the ChemFET. The gate electrode may be used to modulate a channel of electrons within silicon sensors by changing a voltage at the gate electrode. As the modulation takes place, the electrical state between the source and gate electrodes is measured to determine a chemical property of the test sample. Specifically, as the gradient of concentration across the ion selective membrane builds up, the current of the ions is measured to determine the chemical property of the test sample. The measure is usually a logarithmic response to the concentration of the ions. The logarithmic response can be increasing or decreasing as the concentration gradient increases or decreases. By changing the chemistry and sensitivity of nitrate selective membrane 1010, different properties of the test sample may be measured.

Figure 10C:
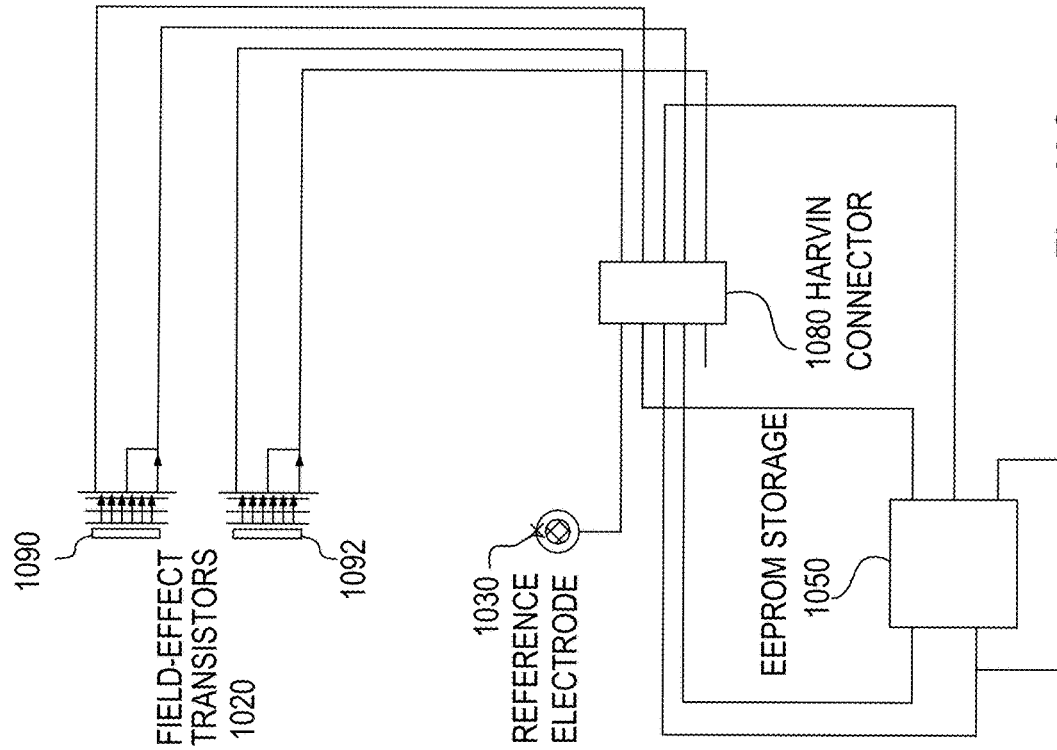
FIG. 10C depicts a schematic view of an example integrated circuit included a sensor cartridge.
Figure 10B:
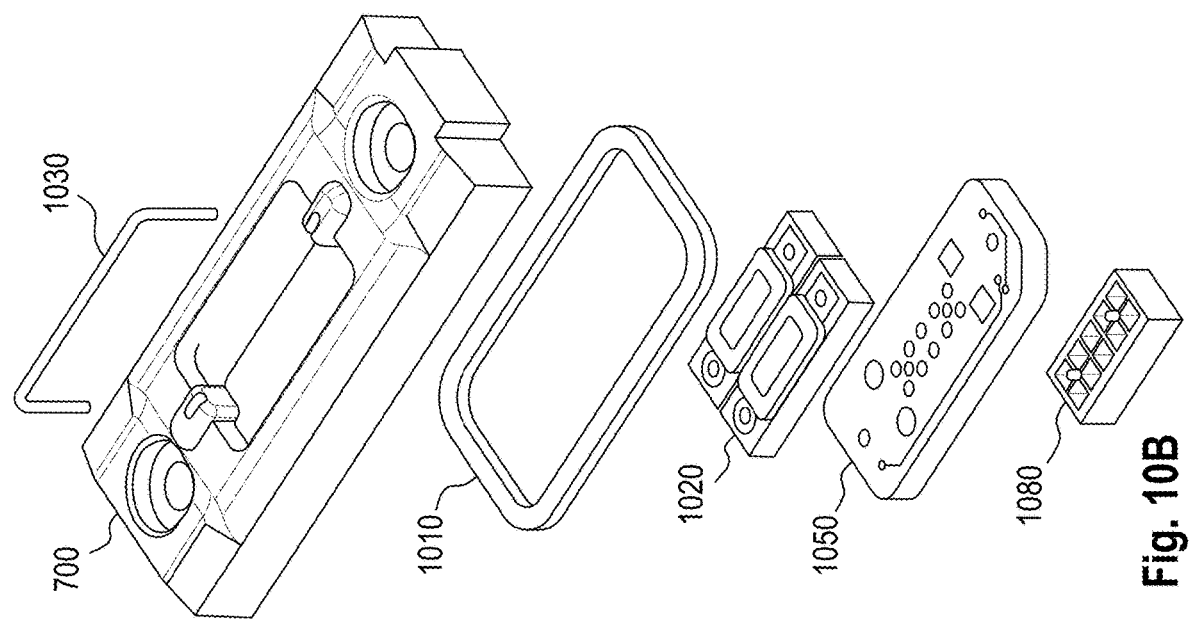
FIG. 10B depicts an exploded view of an example sensor cartridge.

FIG. 10B depicts an exploded view of an example sensor cartridge 700. In the depicted example, sensor cartridge 700 includes nitrate selective membrane 1010, FET 1020, micro-reference electrode 1030, EEPROM storage 1050, and a 10-pin Harwin connector 1080.

Sensor cartridge 700 may also include additional elements that are not depicted in FIG. 10B. For example, while not depicted in FIG. 10B, sensor cartridge 700 may also include temperature diode 1040, computer processor 706 and internal or external power source 720, all depicted in FIG. 10A.

In an embodiment, micro-reference electrode 1030 may be implemented as a gold wire reference placed in front of FET 1020.

FIG. 10C depicts a schematic view of an example integrated circuit included in sensor cartridge 700. The example circuit includes two FETs 1090 and 1092 that collectively correspond to FET 1020 depicted in FIG. 10B. The example circuit also includes micro-reference electrode 1030, EEPROM storage 1050, a 10-pin Harwin connector 1080, and the connections between the components. For the clarity of the schematics, additional components of the sensor cartridge have been omitted.

The example integrated circuit depicted in FIG. 10C is one of many possible integrated circuits that may be used to implement a cartridge-based sensor system for monitoring properties of field soils and wastewater.

5. Extensions and Alternatives

Figure 11:
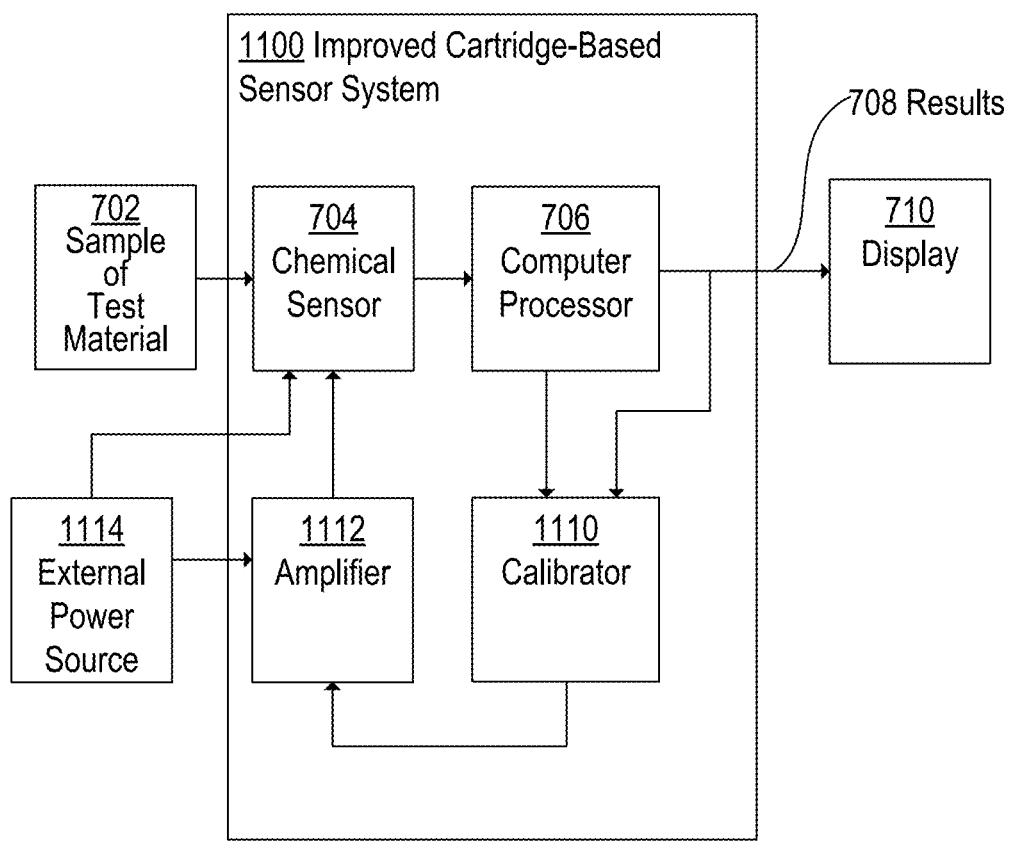
FIG. 11 depicts an example embodiment of an improved cartridge-based sensor system for determining property concentration in soil or water samples.

FIG. 11 depicts an example embodiment of an improved cartridge-based sensor system for determining property concentration in soil or water samples. In an embodiment, improved cartridge-based sensor system 1100 implements a calibration feedback loop which allows an amplifier 1112 to calibrate a sensitivity range of chemical sensor 704. Such a feedback loop may not be available in the sensor systems described previously. The calibration may be performed based on information provided by a calibrator 1110, which may receive input information from computer processor 706. Calibrator 1110 may receive, for example, concentration level readings determined by computer processor 706 and chemical sensor 704, and based on the received information, calibrator 1110 may generate input to amplifier 1112. Upon receiving the input, amplifier 1112 may use the input to modulate, by either increasing or decreasing, the electrical charge provided by, for example, external power source 1114. The resulting modified power charge is supplied to chemical sensor 704 to improve the sensitivity range of chemical sensor 704.

In some embodiments, calibrator 1110 and amplifier 1112 are incorporated into improved sensor cartridge 1100, and thus are part of a silicon chip enclosed in cartridge 1100. In other embodiments (not depicted in FIG. 11), calibrator 1110 and amplifier 1112 are separate from cartridge 1100 and communicate with cartridge 1100 via communications connections and links.

In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

6. Benefits of Certain Embodiments

In an embodiment, a cartridge-based sensor system for monitoring properties of field soils and wastewater is presented. The sensor system is implemented in an integrated silicon chip. The versatility and convenience of the cartridge-based system allow overcoming the shortcomings of conventional systems that require sending soil/water samples to laboratories and awaiting the results for some time. The portable, cartridge-based sensor system also overcomes the inconvenience of using litmus-type test strips to test the properties of the soil.

Embodiments may provide the benefits of convenient and accurate monitoring property concentration in fields at any time. Since some soil properties change in time, monitoring properties of field soil using a portable, the cartridge-based sensor system allows tracking the changes with a high level of accuracy.

Embodiments may provide the benefits of helping farmers and researchers to monitor properties of field soils and wastewater at any location and at any time. The information obtained by the cartridge-based sensor systems may be used to generate accurate graphical representations of properties in the fields. The information may be also used to determine agricultural practices for the fields to achieve desirable yield results. For example, the information may be used to optimize agricultural practices for the fields, and implementations of the optimized practices may lead to increased productivity and yields from the fields. The information may be used to determine, for example, optimum amounts of fertilizers for the field, and optimum schedules for applying the fertilizers at the right field plots and at the right times.

What is claimed is:

1. A sensor system for monitoring properties of field soils and wastewater, the sensor system comprising:
   a cartridge system implemented with an integrated circuit, the cartridge system comprising:
   a chemical sensor including a chemically-sensitive field effect transistor (ChemFET) and a micro-reference electrode;
   the chemical sensor configured to receive a sample of a test material;
   the chemical sensor configured to detect the sample of the test material;
   the chemical sensor configured to determine, based on the ChemFET and micro-reference electrode interacting with the detected sample of the test material, a measure of a property in the test material;
   a computer processor that is coupled to the chemical sensor and that is configured to receive, from the chemical sensor, the measure of the property in the test material;
   the computer processor configured to compute, based on, at least in part, the measure of the property in the test material, a concentration level of the property in the test material;
   the computer processor configured to generate an output that includes the concentration level of the property in the test material; and
   a transmitter that is coupled to the chemical sensor and the computer processor;
   the transmitter configured to establish a communications connection with at least one computer device and to communicate the output to the at least one computer device.

2. The sensor system of claim 1, further comprising an agricultural machine including the at least one computer device; and
   wherein the at least one computer device uses the output to control the at least one agricultural machine as the at least one agricultural machine performs agricultural tasks in an agricultural field.

3. The sensor system of claim 1, wherein calculating the concentration level of the property in the test material includes calculating a concentration level of nitrate.

4. The sensor system of claim 1, wherein the test material is any of: soil, wastewater, standing water, or irrigation system water.

5. The sensor system of claim 1, wherein the cartridge system implemented in the integrated circuit is integrated in any of: a soil probe system, a wastewater monitoring system, an irrigation monitoring system, an on-the-go monitoring system, or a handheld spot measurement system.

6. The sensor system of claim 1, wherein the micro-reference electrode includes an ion selective electrode ("ISE").

7. The sensor system of claim 1, wherein the chemical sensor includes a nitrate selective membrane in communication with the ChemFET, and wherein the nitrate selective member is configured to cause an electrochemical response; and
   wherein the ChemFET is configured to measure the electrochemical response as a direct log function of a concentration of nitrate at a surface of the nitrate selective membrane.

8. The sensor system of claim 1, wherein the cartridge system implemented in the integrated circuit is installed in any of: a field soil probe, a handheld device, a soil sampler, an on-the-go system, or water lines; wherein the water lines include one or more of: tile lines, irrigation lines, or wastewater effluent collection lines.

9. The sensor system of claim 1, wherein the cartridge system implemented in the integrated circuit is installed in a sealed housing that protects the chemical sensor from ingress of moisture and dust; wherein the sealed housing is installed on a measurement platform.

10. A computer-implemented method for determining properties of field soils and wastewater, the method comprising:
receiving, by a chemical sensor of a cartridge system implemented with an integrated circuit, a sample of a test material;
detecting, by the chemical sensor, the sample of the test material;
determining, by the chemical sensor, based on a chemically-sensitive field effect transistor (ChemFET) and a micro-reference electrode of the chemical sensor interacting with the detected sample of the test material, a measure of a property in the test material;
receiving, by a computer processor of the cartridge system implemented in an integrated circuit, from the chemical sensor, the measure of the property in the test material;
calculating, by the computer processor, based on, at least in part, the measure of the property in the test material, a concentration level of the property in the test material;
generating, by the computer processor, an output that includes the concentration level of the property in the test material.

11. The method of claim 10, further comprising:
transmitting the output to at least one computer device configured on at least one agricultural machine; and
controlling the at least one agricultural machine, based on the output, as the at least one agricultural machine performs agricultural tasks in an agricultural field.

12. The method of claim 10, wherein calculating the concentration level of the property in the test material includes calculating a concentration level of nitrate.

13. The method of claim 10, wherein the test material is any of: soil, wastewater, standing water, or irrigation system water.

14. The method of claim 10, wherein the cartridge system implemented in the integrated circuit is integrated in any of: a soil probe system, a wastewater monitoring system, an irrigation monitoring system, an on-the-go monitoring system, or a handheld spot measurement system.

15. The method of claim 10, wherein the micro-reference electrode includes an ion selective electrode ("ISE").

16. The method of claim 10, wherein determining the measure of the property in the test material comprises:
causing, by a nitrate selective member, an electrochemical response; and
measuring, by the ChemFET, the electrochemical response as a direct log function of a concentration of nitrate at a surface of a nitrate selective membrane.

17. The method of claim 10, wherein the cartridge system implemented in the integrated circuit is installed in any of: a field soil probe, a handheld device, a soil sampler, an on-the-go system, or water lines; wherein the water lines include one or more of: tile lines, irrigation lines, or wastewater effluent collection lines.

18. The method of claim 10, wherein the cartridge system implemented in the integrated circuit is installed in a sealed housing that protects the chemical sensor from ingress of moisture and dust; wherein the sealed housing is installed on a measurement platform.

* * * * *